(12) United States Patent
Elliot

(10) Patent No.: US 11,166,829 B2
(45) Date of Patent: Nov. 9, 2021

(54) INTRAMEDULLARY CUTTING DEVICE FOR REVISION HIP ARTHROPLASTY

(71) Applicant: THINK SURGICAL, INC., Fremont, CA (US)

(72) Inventor: Gibson Elliot, Fremont, CA (US)

(73) Assignee: THINK SURGICAL, INC., Fremont, CA (US)

( * ) Notice: Subject to any disclaimer, the term of this patent is extended or adjusted under 35 U.S.C. 154(b) by 174 days.

(21) Appl. No.: 16/620,536

(22) PCT Filed: Jun. 12, 2018

(86) PCT No.: PCT/US2018/037021
§ 371 (c)(1),
(2) Date: Dec. 9, 2019

(87) PCT Pub. No.: WO2018/231775
PCT Pub. Date: Dec. 20, 2018

(65) Prior Publication Data
US 2020/0222206 A1 Jul. 16, 2020

Related U.S. Application Data

(60) Provisional application No. 62/518,409, filed on Jun. 12, 2017.

(51) Int. Cl.
*A61B 17/58* (2006.01)
*A61B 17/60* (2006.01)
(Continued)

(52) U.S. Cl.
CPC .......... *A61F 2/461* (2013.01); *A61B 17/1675* (2013.01); *A61B 34/20* (2016.02);
(Continued)

(58) Field of Classification Search
CPC combination set(s) only.
See application file for complete search history.

(56) References Cited

U.S. PATENT DOCUMENTS 7,632,277 B2 12/2009 Woll et al.
2002/0091391 A1 7/2002 Cole et al.
(Continued)

FOREIGN PATENT DOCUMENTS

JP 2007-530221 A 11/2007

OTHER PUBLICATIONS

Int'l. Search Report for PCT/US2018/037021, dated Sep. 13, 2018.

*Primary Examiner* — Sameh R Boles
(74) *Attorney, Agent, or Firm* — Blue Filament Law PLLC

(57) ABSTRACT

A cutting device is provided that includes an expandable tube having a base and a hollow interior for receiving the implant therein. The expandable tube includes cutting segments extending from the base and terminating to form a distal end of the expandable tube. At least one of the cutting segments has a cutting end with cutting teeth at the distal end of the expandable tube. Spring shaped sections are provided that extend the cutting segments. A method for removing an implant from a target bone is also provided based on the cutting device. A system for removing material directly surrounding an outer surface of an implant in an intramedullary canal of a target bone is also provided based on the cutting device and a sheath. A retractable opening is formed of leaflets at a distal end of the sheath, and a proximal end opposite the distal end.

10 Claims, 17 Drawing Sheets

(51) Int. Cl.
*A61F 2/00* (2006.01)
*A61F 2/46* (2006.01)
*A61B 34/20* (2016.01)
*A61B 34/30* (2016.01)
*A61B 17/16* (2006.01)
*A61B 34/10* (2016.01)
*A61B 34/00* (2016.01)
*A61B 17/00* (2006.01)
*A61B 17/56* (2006.01)
*A61F 2/30* (2006.01)

(52) U.S. Cl.
CPC ............ *A61B 34/30* (2016.02); *A61B 17/164* (2013.01); *A61B 17/1626* (2013.01); *A61B 17/1637* (2013.01); *A61B 17/1664* (2013.01); *A61B 2017/00398* (2013.01); *A61B 2017/00867* (2013.01); *A61B 2017/00973* (2013.01); *A61B 2017/564* (2013.01); *A61B 2034/105* (2016.02); *A61B 2034/2051* (2016.02); *A61B 2034/2055* (2016.02); *A61B 2034/742* (2016.02); *A61B 2034/743* (2016.02); *A61B 2034/744* (2016.02); *A61B 2217/005* (2013.01); *A61F 2/4607* (2013.01); *A61F 2002/3069* (2013.01); *A61F 2002/4619* (2013.01); *A61F 2002/4628* (2013.01)

(56) References Cited

U.S. PATENT DOCUMENTS

2003/0073998 A1 4/2003 Pagliuca et al.
2007/0123995 A1 5/2007 Thelen et al.
2011/0319898 A1 12/2011 O'Neil et al.

S110: cut an opening into an intramedullary canal of the knee

S120: insert a cutting device into the intramedullary canal to reach a portion of an implant located inside the intramedullary canal S130: rotate the cutting device to remove material around the implant S140: remove the implant from the target bone

FIG. 2

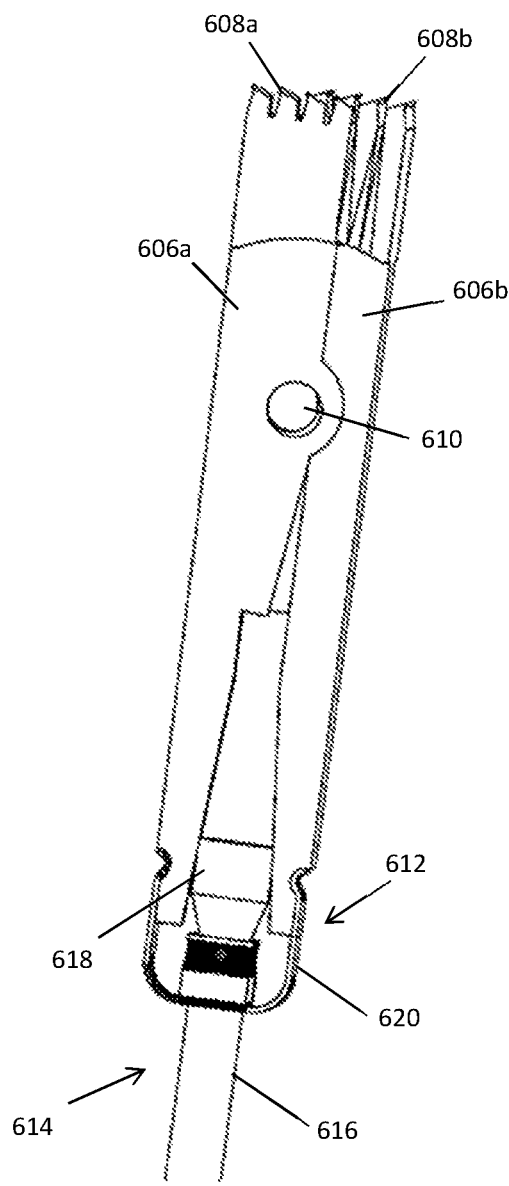
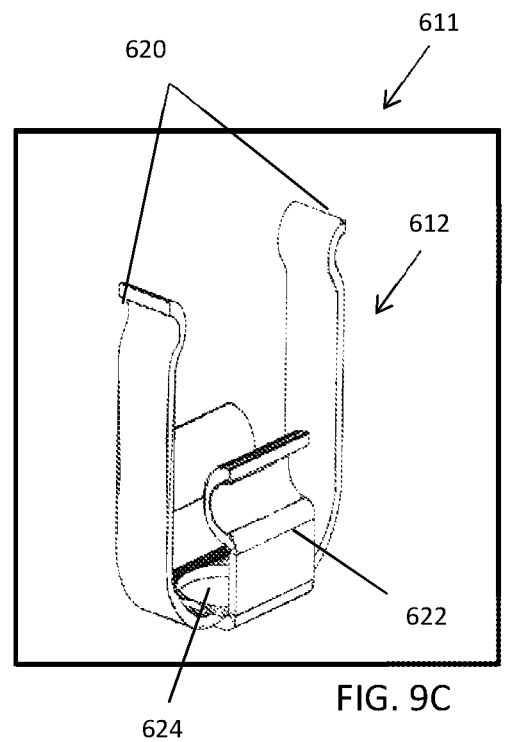
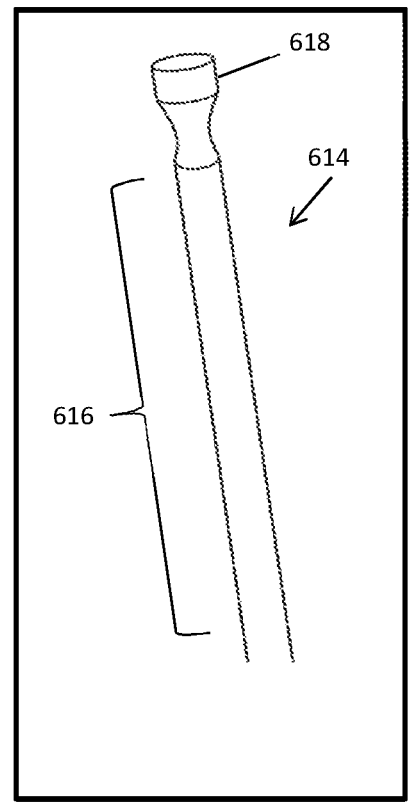
FIG. 9B
FIG. 9C
FIG. 9D

```
S210: receive scan data of a patient's target bone
          ↓
S220: create virtual three-dimensional model of patient's bone
          ↓
S230: identify a site to enter the intramedullary canal of knee
          ↓
S240: register the location of the target bone and knee intraoperatively in the robot's workspace
          ↓
S250: robotically mill the target bone
          ↓
S260: insert the cutting device inside the target bone
          ↓
S270: robotically cut material around the implant
          ↓
S280: remove the implant from the target bone
```

FIG. 11

INTRAMEDULLARY CUTTING DEVICE FOR REVISION HIP ARTHROPLASTY

RELATED APPLICATION DATA

This application is a 371 continuation of International Patent Application No. PCT/US2018/037021, filed on Jun. 12, 2018, which, in turn, claims the benefit of U.S. Provisional Application No. 62/518,409, filed on Jun. 12, 2017; the contents of which are hereby incorporated by reference.

FIELD OF THE INVENTION

The present invention in general, relates to revision orthopedic surgery, and more particularly to a new and useful system and method for planning and executing the removal of an implant in revision hip and knee surgery.

BACKGROUND OF THE INVENTION

Joint arthroplasty is a well-known surgical procedure by which a diseased and/or damaged natural joint is replaced with a prosthetic joint. Joint arthroplasty is commonly performed for hips, knees, elbows, and other joints. Hip arthroplasty includes the insertion of a prosthetic femoral stem component into the intramedullary canal of the femur. A ball or head associated with the end of the stem articulates within a patient's natural acetabulum, or a prosthetic acetabular component fitted within the acetabulum of the patient in the case of total hip arthroplasty.

It is important that the femoral stem be securely positioned within the femur so as to achieve adequate initial fixation, as well to promote long term stability of the implant. Femoral components can have various design characteristics to provide optimal fixation properties, such as surface features for encouraging bony ingrowth, tailored flexibilities for reducing stress shielding, and particular surface properties for controlling adhesion to cement. While such femoral components may extend the useful life of the implant, a surgical revision of the prosthesis may become necessary after an extended period of time.

One problem associated with the revision of a femoral component is the difficulty of removing the primary implant along the longitudinal axis of the femur. For example, FIG. 1 depicts a cross-sectional view of a femoral hip implant 100 fixed inside an intramedullary canal (IC) of a femur F. The femoral hip implant 100 generally includes a femoral head 102, and a femoral stem 104 having a distal tip 106. The femoral head 102 articulates with the acetabulum component, while the femoral stem 104 is fixed inside the intramedullary canal (IC). During revision hip arthroplasty the user disconnects the acetabulum (A) from the femur (F) and removes the implant 100 from the intramedullary canal (IC). However, the implant 100 may be rigidly fixed in the intramedullary canal (IC) making the removal of the implant 100 quite difficult. The difficulty in removing the implant is generally attributed to the rigid fixation of the stem 104 in the femur due to cement fixation, osseointegration fixation, or impaction.

Surgeons currently use techniques such as chipping away at material 108 (e.g., cement, bony ingrowth) surrounding the stem 104, performing trochanteric osteotomies, or using slap hammers to forcibly remove the stem 104 from the femur (F). However, these techniques are labor intensive, imprecise and can damage the surrounding anatomy.

Thus, there is a need in the art for a system and method to more efficiently remove an implant from a bone during orthopedic revision procedures.

BRIEF DESCRIPTION OF THE DRAWINGS

Examples illustrative of embodiments are described below with reference to figures attached hereto. In the figures, identical structures, elements or parts that appear in more than one figure are generally labeled with a same numeral in all the figures in which they appear. Dimensions of components and features shown in the figures are generally chosen for convenience and clarity of presentation and are not necessarily shown to scale. The figures are listed below.

FIG. 2 is a flowchart depicting an inventive method for manually removing an implant from a bone with a cutting device in accordance with embodiments of the invention;

FIG. 4A depicts a perspective view of the cutting device, FIG. 4B depicts a magnified proximal end view thereof, FIG. 4C depicts an orthogonal perspective view thereof relative to FIG. 4A, and FIG. 4D depicts magnified proximal end view of FIG. 4C;

FIG. 8A depicts a perspective view of the retractor inside the sheath, FIG. 8B depicts the retractor and sheath inside an intramedullary canal in non-retracted state, and FIG. 8C depicts the retractor and sheath inside an intramedullary canal of in a retracted state;

FIGS. 9A-9F depict an inventive cutting device for cutting material directly surrounding an implant, where FIG. 9A is a perspective view of the cutting device, FIG. 9B depicts internal components of the cutting device, FIGS. 9C and 9D depict enlarged view of internal components of FIG. 9B, FIG. 9E depicts the cutting device used to remove a femoral hip implant, and FIG. 9F depicts the cutting device used to remove knee implants;

FIG. 10A depicts the device in an unactuated state, and FIG. 10B depicts the device in an actuated state.

FIG. 11 is a flowchart depicting a method for robotically removing an implant from a bone with a cutting device in accordance with embodiments of the invention.

DETAILED DESCRIPTION OF THE INVENTION

Figure 1:
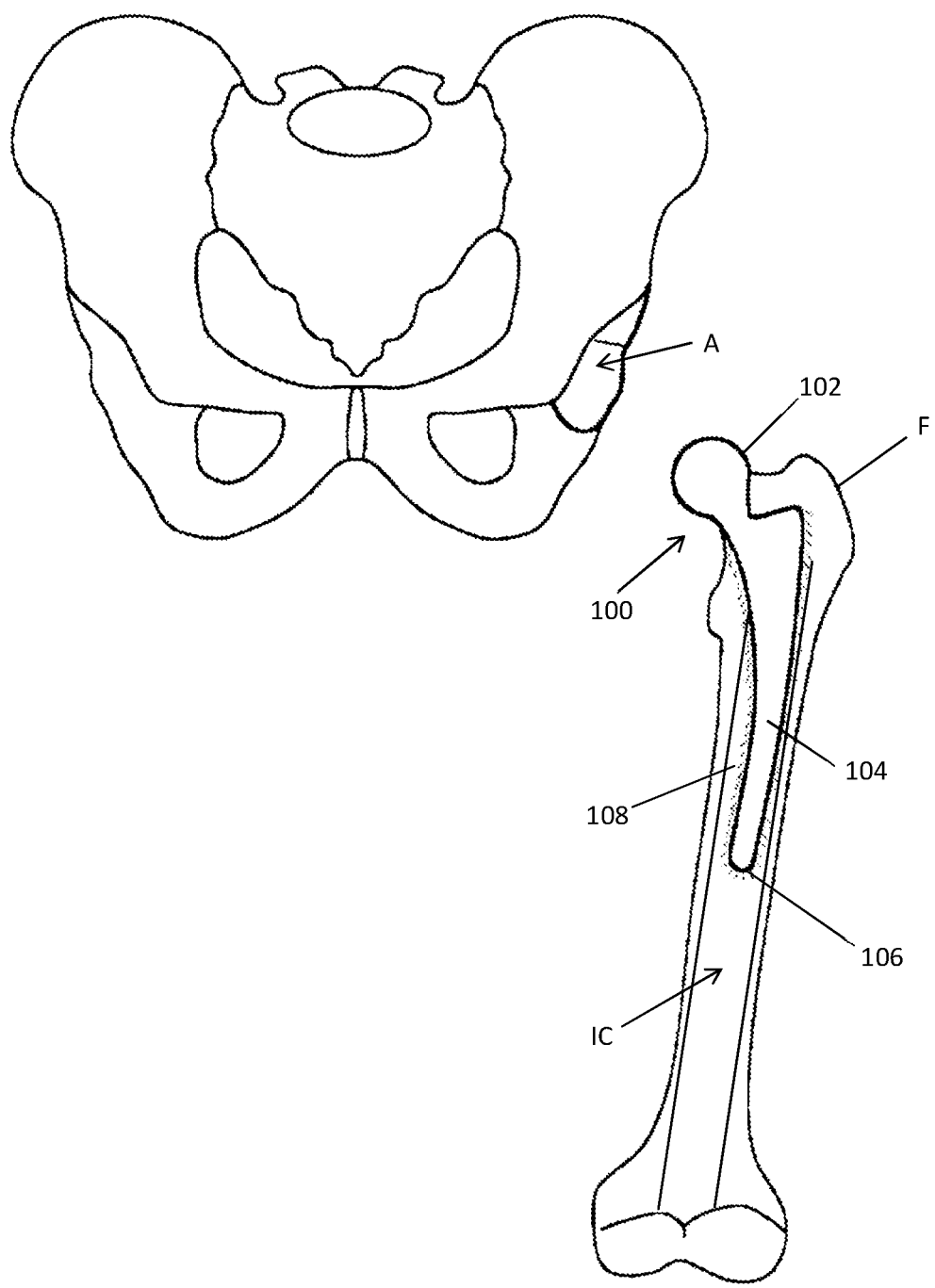
FIG. 1 depicts a prior art example of an implant fixed in an intramedullary canal of a femur.

The present invention will now be described with reference to the following embodiments. As is apparent by these descriptions, this invention can be embodied in different forms and should not be construed as limited to the embodiments set forth herein. Rather, these embodiments are provided so that this disclosure will be thorough and complete, and will fully convey the scope of the invention to those skilled in the art. For example, features illustrated with respect to one embodiment can be incorporated into other embodiments, and features illustrated with respect to a particular embodiment may be deleted from that embodiment. In addition, numerous variations and additions to the embodiments suggested herein will be apparent to those skilled in the art in light of the instant disclosure, which do not depart from the instant invention. Hence, the following specification is intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents, and other references mentioned herein are incorporated by reference in their entirety.

Definitions

Unless indicated otherwise, explicitly or by context, the following terms are used herein as set forth below.

As used in the description of the invention and the appended claims, the singular forms "a," "an" and "the" are intended to include the plural forms as well, unless the context clearly indicates otherwise.

Also, as used herein, "and/or" refers to and encompasses any and all possible combinations of one or more of the associated listed items, as well as the lack of combinations when interpreted in the alternative ("or").

As used herein, the term "registration" refers to the determination of the spatial relationship between two or more objects or coordinate systems such as a computer-assist device and at least one of a bone, or an image data set of a bone.

As used herein, the term "target bone" refers to a bony structure in need of a surgical procedure, treatment, repair or any combination thereof.

While the present invention is illustrated visually hereafter with respect to a femur as an example of the target bone for which the present invention is applied, it is appreciated that the present invention is equally applicable to other bones of a human, non-human primate, or other mammals.

Furthermore, it should be appreciated that while the systems and methods described herein teach the removal of a femoral implant in revision hip arthroplasty, any of a wide variety of different bone implants may likewise be removed according to the teaching of this invention (e.g., a knee implant and shoulder implant). It is further contemplated that the system and method may be useful for the precise cutting of material around other external objects in the industrial, carpentry, or other medical fields.

Manual Intramedullary Canal Cutting Procedure

Embodiments of the present invention describe a method and system for removing an implant from a bone. With reference to FIG. 2, a specific embodiment of a method for removing a femoral implant is shown. The method includes the steps of (a) cutting an opening into the intramedullary canal of the femur (S110) (b) inserting a cutting device into the intramedullary canal to reach a portion of an implant located inside the intramedullary canal (S120) (c) rotating the cutting device to remove material around the implant (S130) and (d) removing the implant from the target bone (S140). Further embodiments of the method and components are further described in details below.

Figure 3:
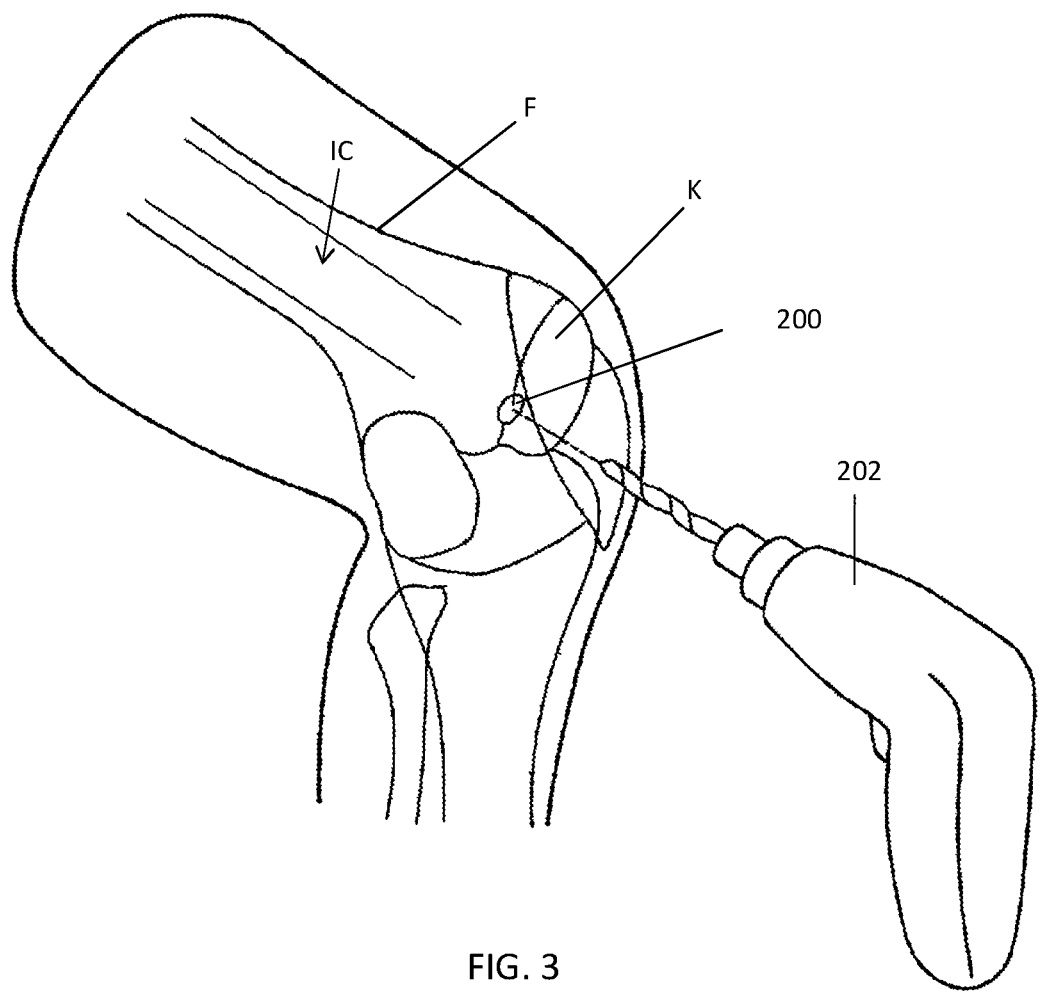
FIG. 3 depicts a drill to create an opening in a bone to gain access to an intramedullary canal in accordance with the present invention.

With respect to FIG. 3, a distal part of a femur (F) and knee (K) is shown as potential areas to create an opening 200 to provide access into the intramedullary canal (IC). While the present invention is illustrated in the context of femoral canal revisions, it is appreciated that the present invention is also suitable in the context of other long bones including the tibia, fibula, metatarsals, metatarsal phalanges, humerus, radius, ulna, metacarpals, and metacarpal phalanges upon accounting thee differences in a bone diameter. The opening 200 is configured to accommodate a cutting device to facilitate the removal of the femoral stem 104 from the femur (F). In a particular embodiment, the opening 200 is created in the center of the knee (K) with the use of a drill 202. However, it should be appreciated that the opening 200 may be created at any position or angle on the femur (F) that is distal to the distal tip 106 of the femoral stem 104 and where the anatomy allows it. Also, the shape and size of the opening 200 may be determined by a user based on the anatomical measurement of each individual patient.

Figure 4A:
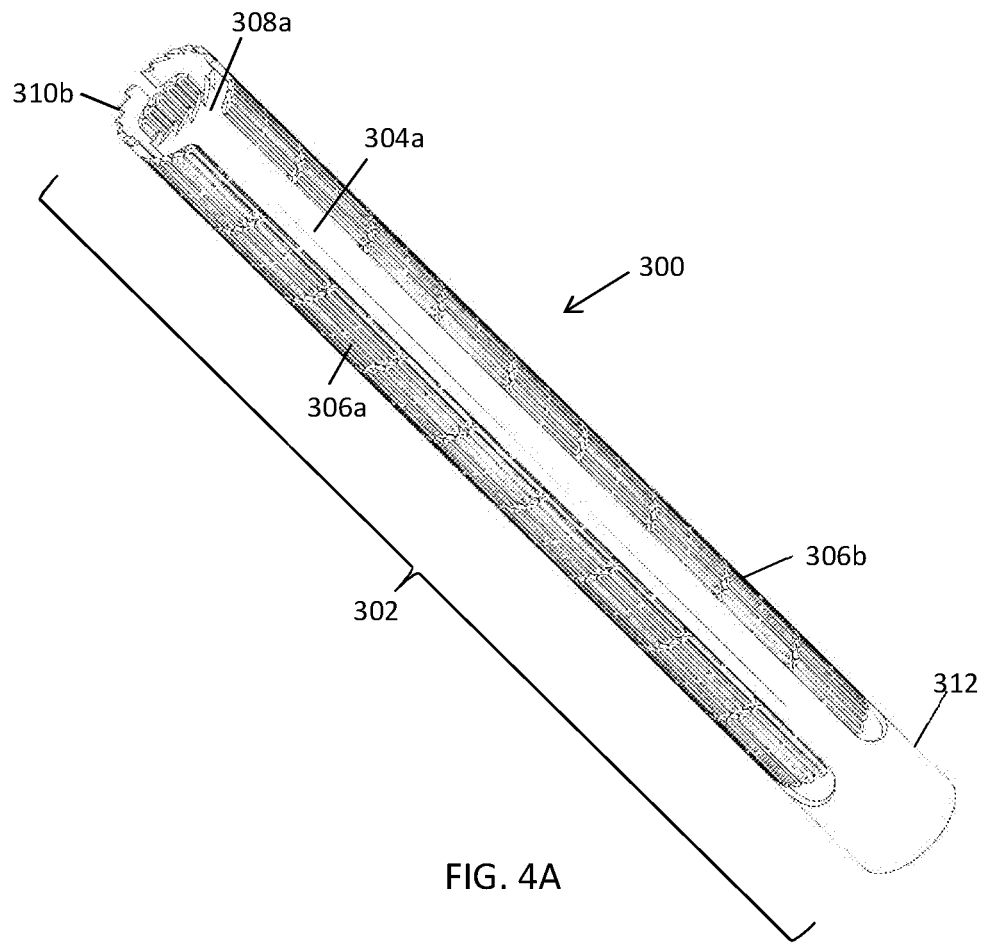
FIGS. 4A-4D depict an inventive cutting device in accordance with embodiments of the invention, where
Figure 4B:
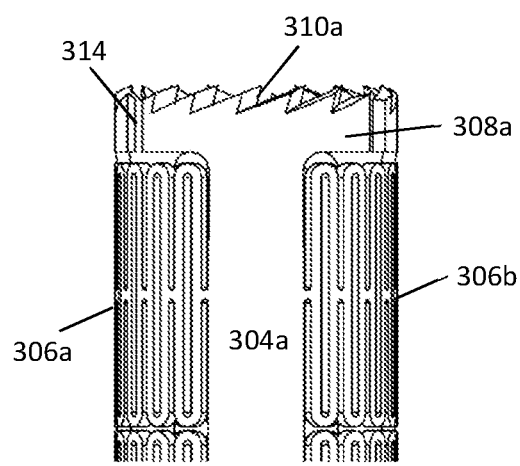
Figure 4C:
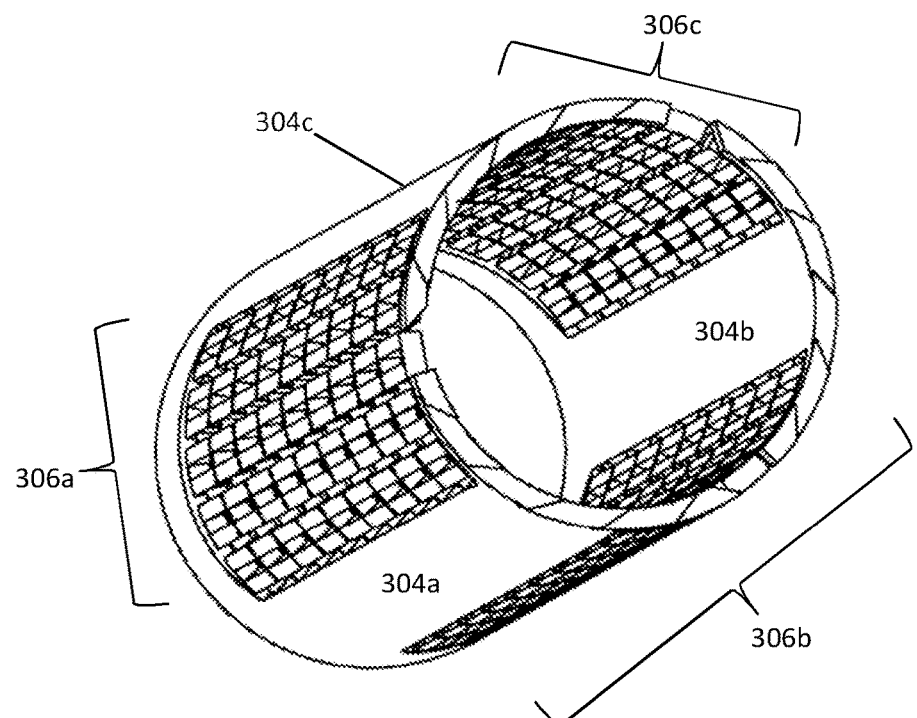
Figure 4D:
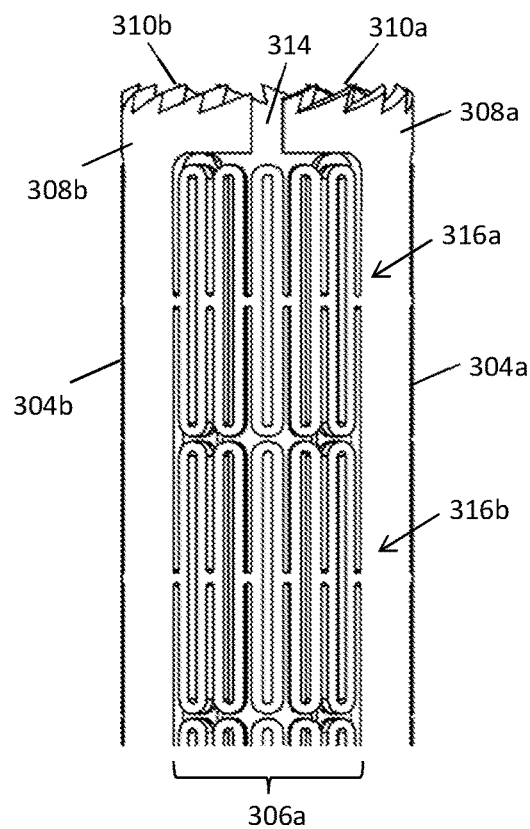

Referring to FIGS. 4A-4D, a specific inventive embodiment of a cutting device 300 for removing material 108 surrounding an implant, such as the femoral hip implant 100, from within an intramedullary canal (IC) is shown. The cutting device 300 is configured to cut, abrade, or otherwise remove material 108 directly surrounding the outer surface of the implant 100 from within the intramedullary canal (IC). The cutting device 300 is further configured to expand and conform to the geometry of the implant 100 as the cutting device 300 is advanced along the length of the implant 100 to ensure that only the material 108 directly surrounding the outer surface of the implant 100 is removed. The cutting device 300 generally includes an expandable tube 302 having a hollow interior for receiving an implant therein. The expandable tube 302 includes at least two cutting segments (304a, 304b, 304c). Each cutting segment (304a, 304b, 304c) is independently in the form of an arcuate elongated shaft, where at least a portion of the cutting segments (304a, 304b, 304c) are coupled together by interspersed spring shaped sections (306a, 306b, 306c) as further described below. Each cutting segment (304a, 304b, 304c) includes a cutting end (308a, 308b, 308c) having a plurality of cutting teeth (310a, 310b, 310c) for chipping, rubbing, or otherwise removing material 108 surrounding the implant. In various embodiments, as best seen in FIG. 4B and FIG. 4D, the cutting ends 308 laterally extend over the spring shaped sections (306a, 306b, 306c) to substantially circumvent around the distal end of the tube 302 to increase the cutting surface area. Here, 'substantially' refers to at least 51 percent of the distance of circumvention around the distal end of the tube 302, where each cutting end (308a, 308b, 308c) is separated by a gap 314. Therefore, each cutting segment (304a, 304b, 304c) acts as individual units to permit the cutting device 100 to expand and conform around an implant. The cutting device 300 may further include a base 312, where each of the cutting portions 304 originate from the base 312 as best seen in FIG. 4A.

FIG. 4D depicts a detailed view of a particular embodiment of the spring shaped sections (306a, 306b, 306c). The spring shaped sections (306a, 306b, 306c) inn some inventive embodiments include a plurality of expandable rows (316a, 316b) where each expandable rows (316a, 316b) acts as a spring. The spring shaped sections (306a, 306b, 306c) allow the interspersed cutting segments (304a, 304b, 304c) to expand and contract relative to one another and therefore conform around the outer surface of the implant 100 as the cutting device 300 is advanced along the length of the implant 100. In various embodiments, the expandable rows (316a, 316b) are in the form of a series of elliptical rings, where the rings are linked to adjacent rings at the center of each ring. In another embodiment, the expandable rows (316a, 316b) are in the form of a traditional coil or spring. It should be appreciated, that the expandable rows (316a, 316b) may be formed of other patterns that create a spring effect. In addition, the length and number of expandable rows (316a, 316b) may be adjusted based on the size of a particular implant to better conform to the geometry of that implant.

In various embodiments, the cutting device 300 is manufactured from a single piece of material and shaped using a plasma or laser cut. For example, as shown in FIG. 4D, the spring shaped section (306a, 306b, 306c) may be directly plasma cut to form a machined spring pattern directly into the cutting device 300. In various embodiments, the material is nitinol (nickel-titanium) chosen for its high strength, super elasticity and biocompatibility which makes it suitable for the purpose of this application. However, it is contemplated that the cutting device 300 may be made from a number of other materials with similar characteristics of a shape memory material or alloys thereof, such as nickel-titanium-cobalt, which have suitable mechanical properties to allow the cutting segments (304a, 304b, 304c) to expand and conform to an implant. In various embodiments, the cutting device 300 has multiple components that are assembled to one another to form the cutting device 300 as further described below.

In a particular embodiment, the spring shaped sections (306a, 306b, 306c) and/or individual expandable rows (316a, 316b) are removable units where the removable units may be removed and inserted between the cutting segments (304a, 304b, 304c). Having removable units may be particularly advantageous for a couple reasons. First, different sizes and shapes of the removable units may be inserted between the cutting segments (304a, 304b, 304c) based on the application of the cutting device 300. Second, worn-out spring shaped sections (306a, 306b, 306c) and/or individual expandable rows (316a, 316b) may be replaced easier without a need to completely replace the entire cutting device 300.

In a particular embodiment, with respect to the plurality of cutting teeth (310a, 310b, 310c), the cutting teeth (310a, 310b, 310c) are configured to cut, rub, or otherwise remove material 108 surrounding an implant while the cutting device 300 is rotated around the implant. The cutting ends (308a, 308b, 308c) may include any number of cutting teeth (310a, 310b, 310c) which may vary in shape, size, and angular orientation based on the particular application of the cutting device 300. In a specific inventive embodiment, the cutting ends (308a, 308b, 308c) and/or cutting teeth (310a, 310b, 310c) may be removably coupled to the cutting segments (304a, 304b, 304c) where the cutting ends (308a, 308b, 308c) and/or cutting teeth (310a, 310b, 310c) are made of a stiffer material than the other components of the cutting device 300. For example, the cutting ends (308a, 308b, 308c) may be made of stainless steel, grade 17-4 PH, for its high strength and resistance to corrosion in which it is suitable for more rigid cuts, while the other components of the cutting device 300 are made of nitinol.

Figure 4E:
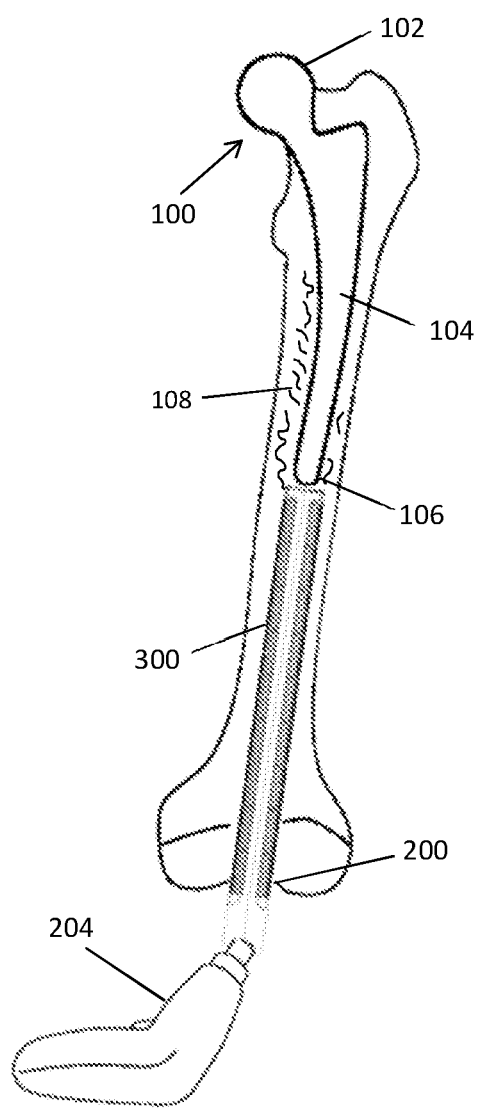
FIG. 4E depicts an inventive cutting device of either FIG. 4A or 4C in the context of cutting around material surrounding an implant located inside an intramedullary canal.

With reference to FIG. 4E, a particular embodiment of using the cutting device 300 for removing a femoral hip implant 100 is shown. The cutting procedure begins by inserting the cutting device 300 in the intramedullary canal (IC) through the opening 200 drilled in the bone as previously mentioned. The cutting device 300 is advanced through the canal (IC) to make contact with the distal tip 106 of the femoral stem 104. The cutting device 300 is then rotated and translated along the length of the stem 104 to remove material 108 surrounding the stem 104. As the device 300 is translated, the stem 104 applies pressure on the hollow interior of expandable tube 302 causing the spring shape sections (306a, 306b, 306c) to expand and the cutting segments (304a, 304b, 304c) to tightly conform to the outer surface of the stem 104. Therefore, only material 108 directly surrounding the stem 104 is cut, rubbed, or otherwise removed. The cutting procedure terminates once the implant 100 can be safely removed from the intramedullary canal (IC). For example, during cutting, the surgeon may apply pressure, by hand or with a slap hammer, on the exposed side of the implant 100, such as the femoral head 102, until the implant 100 releases from the bone, at which time the cutting can terminate.

The cutting device 300 may be rotated by a drill 204, motor, or other actuating mechanism. In various embodiments, the base 312 of the cutting device 300 may be configured to couple directly to the drill 204, where the drill 560 drives the cutting device 300. In another embodiment, a distal end of a drive shaft (not shown) is attached to the cutting device 300 and a proximal end of the drive shaft is attached to a drill 204, motor, or other actuator. The drive shaft may be attached on the inside of the tube 302 at the base 312. In a particular embodiment, the distal end of the drive shaft includes two or more prongs, the number of prongs based on the number of cutting segments (304a, 304b, 304c), where each individual prong attaches inside the tube 302 on each individual cutting segment (304a, 304b, 304c). The prongs may be further configured to attach at an angle so as to permit the prongs to expand and collapse with the cutting segments (304a, 304b, 304c) and still rotate the cutting device 300 during the cutting procedure. A flexible sleeve may be present around the drive shaft to protect the surrounding anatomy while driving the cutting device 300. To translate the cutting device 300 along the length of the implant 100, a user may apply pressure on the drill. In other embodiments, the cutting device 300 is rotated and translated by a computer-assisted surgical system as described below. In yet another embodiment, the cutting device 300 is manually rotated and translated.

In various embodiments, the base 312 of the cutting device 300 is coupled to a vacuum device mechanism where the vacuum device is configured to intake the material 108 during the cutting procedure.

Figure 5:
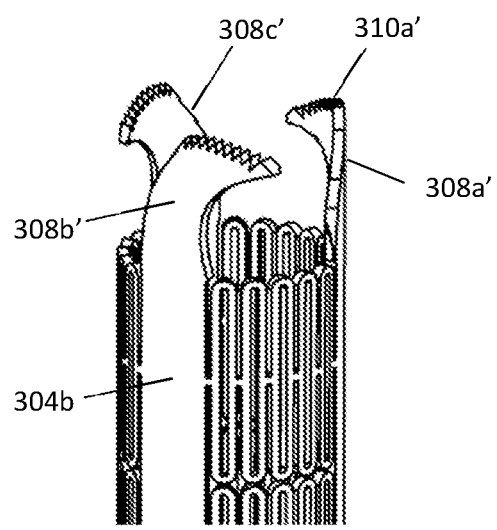
FIG. 5 depicts an inventive cutting device having a cutting end to account for cutting deflection in accordance with embodiments of the invention.

With reference to FIG. 5, a specific inventive embodiment of a plurality of deflective cutting ends (308a', 308b', 308c') is shown that may account for deflection experienced on the cutting ends (308a', 308b', 308c') during cutting. The frictional forces created during cutting may cause the cutting ends (308a', 308b', 308c') to deflect, which may decrease cutting efficiency; therefore, the deflective cutting ends (308a', 308b', 308c') are configured to permit the removal of material 108 around the implant 100 if the cutting ends (308a', 308b', 308c') deflects during the cutting procedure. In a particular embodiment, the deflective cutting ends (308a', 308b', 308c') are in the form of a hook, or otherwise curved in shape. A plurality of cutting teeth (310a', 310b', 310c') are positioned and angled on the deflective cutting ends (308a', 308b', 308c') to remove the material 108 while the deflective cutting ends (308a', 308b', 308c') deflect during the cutting procedure.

Figure 6:
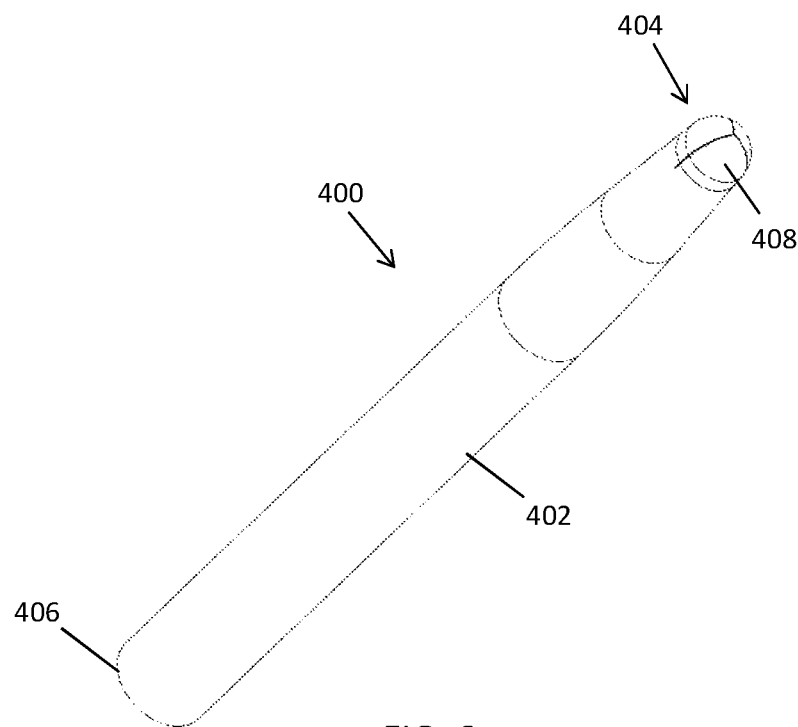
FIG. 6 depicts a perspective view of a sheath for use during a revision procedure through an intramedullary canal in accordance with embodiments of the invention.

With reference to FIG. 6, various embodiments of a sheath 400 used in conjunction with the cutting device 300 is shown. The sheath 400 serves several purposes including protecting surrounding tissue during cutting, as well as aid in the removal of bone marrow if desired as further described below. In a particular embodiment, the sheath 400 includes a hollow cylindrical body 402, a retractable opening 404, and a proximal end 406. The hollow cylindrical body 402 is dimensioned to receive the cutting device 300 therein. The retractable opening 404 may include at least two leaflets 408 having a smooth semi-spherical surface. The retractable opening 404 is configured to open when an external object such as the cutting device 300 forces the leaflets open as the cutting device 300 is passed through the interior side of the cylindrical body 402 and out the opening 404. A particular use of the sheath 400 is to protect anatomical structures inside the intramedullary canal while the cutting device 300 rotates and removes material surrounding the implant 300. Prior to cutting around the implant, the sheath 400 with the cutting device 300 therein may be positioned just distal of the femoral stem 320. The cutting device 300 is then pushed out through the retractable opening 404 and advanced along the length of the implant 100. Therefore, the sheath 400 may protect all of the structures distal to the distal tip 106 of the femoral stem 104. Additionally, one of the advantages of using a sheath 400 with the cutting device 300 is that, the smooth surface of the semi-spherical retractable opening 404 further prevents/reduces damage to the structures in the intramedullary canal (IC) as the sheath 400 is advanced through the intramedullary canal (IC).

Figure 7:
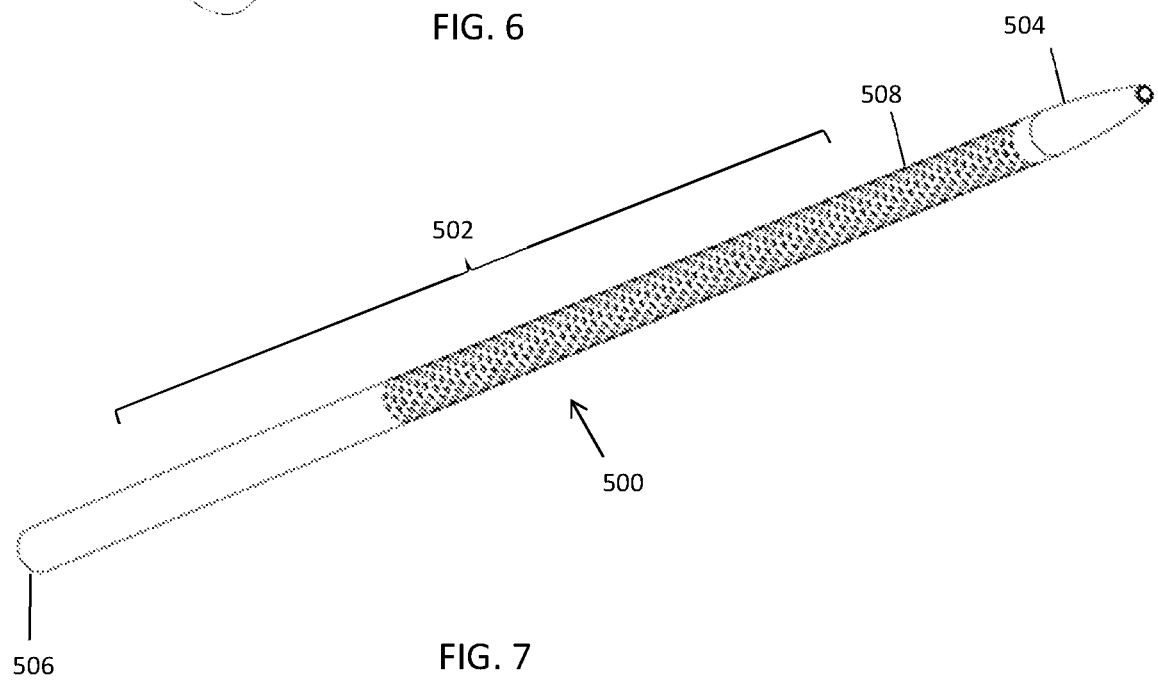
FIG. 7 depicts a bone marrow retractor for collecting bone marrow inside an intramedullary canal in accordance with embodiments of the invention.

With reference to FIG. 7, various embodiments of a bone marrow retractor 500 to collect the bone marrow before the insertion of the cutting device 300 in the intramedullary canal (IC) is shown. The bone marrow retractor 500 includes a hollow cylindrical body 502 having a top end 504, a bottom end 506, and a plurality of openings 508 dispersed on the cylindrical body 505 to act as a sieve. The bone marrow retractor 500 is configured to insert inside the intramedullary canal (IC) and collect the bone marrow through the plurality of openings 508. The pressure gradient between the hollow interior of the cylindrical body 502 and the intramedullary canal (IC) allows for the collection of the bone marrow. The collected bone marrow is then stored in the interior volume of the hollow cylindrical body 502. The bone marrow retractor 500 is advantageous for several reasons. First, due to the shape and form of the retractor 500, the surrounding architecture and anatomy is protected during the collection of the bone marrow. Second, the bone marrow may be preserved during the cutting procedure giving the user the option to replace the bone marrow after the revision procedure is complete. In some instances, the user may treat the bone marrow outside the patient's anatomy with growth factors, healing agents, stimulants, and/or anti-coagulation factors prior to returning the bone marrow into the intramedullary canal. In some embodiments, the user may replace the intramedullary canal with a desirable substance other than the bone marrow and/or simply discard the bone marrow altogether depending on the preferences of the user.

Figure 8A:
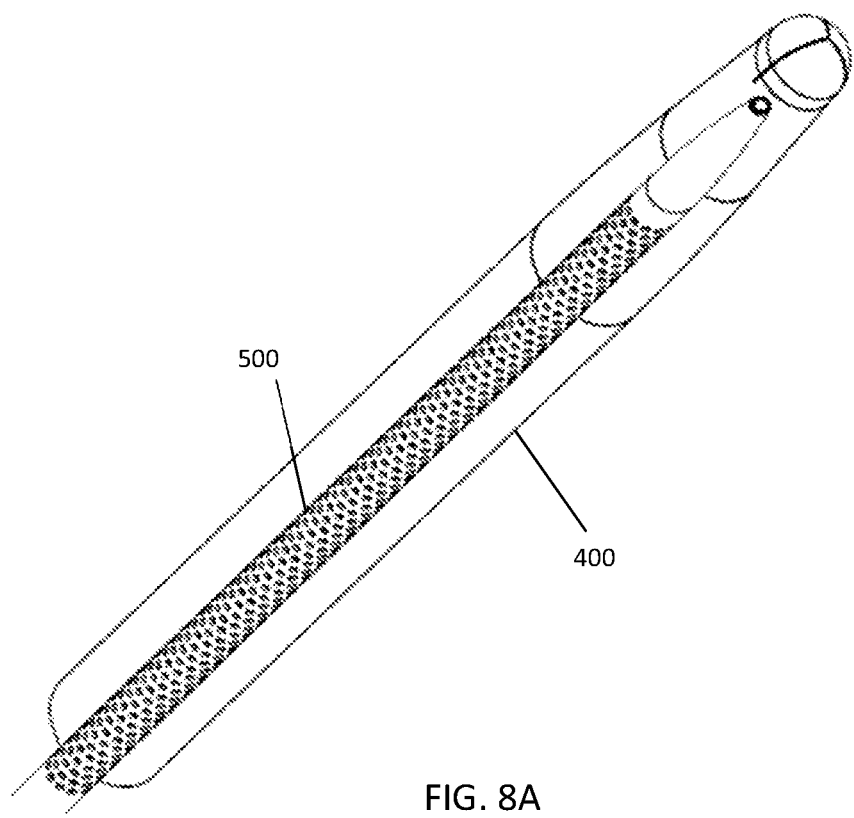
FIGS. 8A-8C depict a bone marrow retractor inside a sheath for retracting bone marrow in accordance with embodiments of the invention, where
Figure 8B:
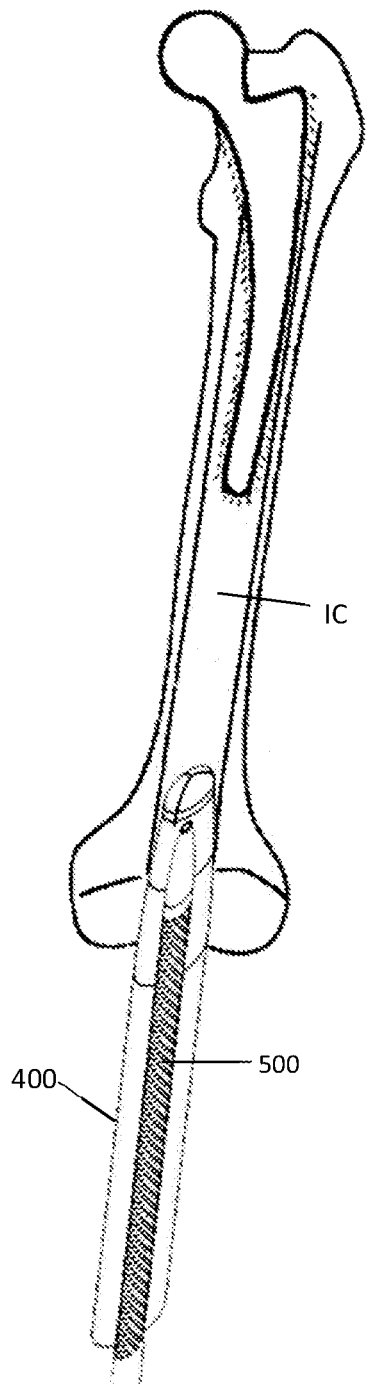
Figure 8C:
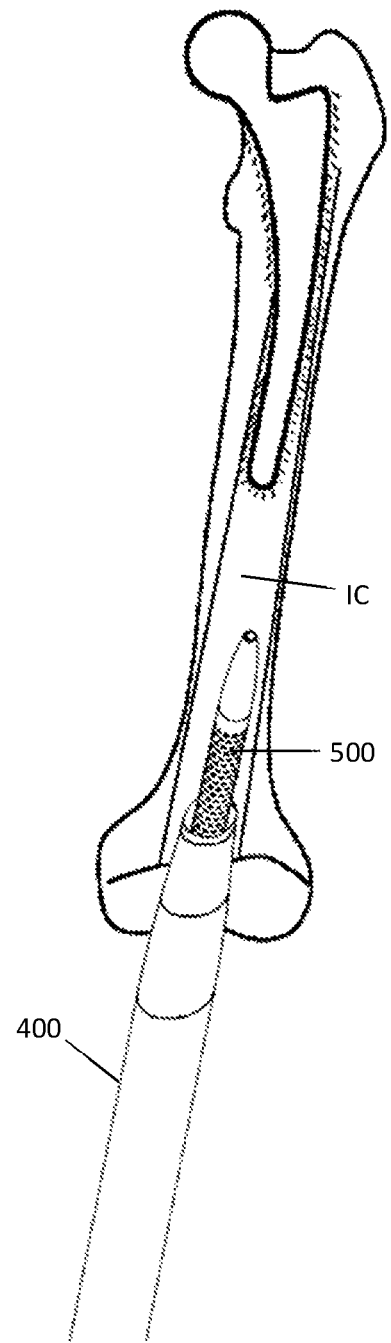

In another embodiment and referring to FIG. 8A, the bone marrow retractor 500 may be inserted in the sheath 400 before introducing into the intramedullary canal (IC). Following the introduction of the sheath 400 into the intramedullary canal (IC), the pressure imposed on the bone marrow from the sheath 400 increases the overall pressure of the bone marrow surrounding the sheath 400. As shown in FIGS. 8B-8C, the user may withdraw the sheath 400 over the bone marrow retractor 500, at which point the bone marrow is absorbed with a higher intensity inside the openings 508 of the bone marrow retractor 500. The use of the bone marrow retractor 500 in conjunction with the sheath 400 is advantageous as the suction effects introduced by the entrance and retraction of the sheath to the intramedullary canal (IC) increase the collection of the bone marrow inside the interior volume of the hollow cylindrical body 502 of the bone marrow retractor 500.

Scissor Cutting Procedure

Figure 9A:
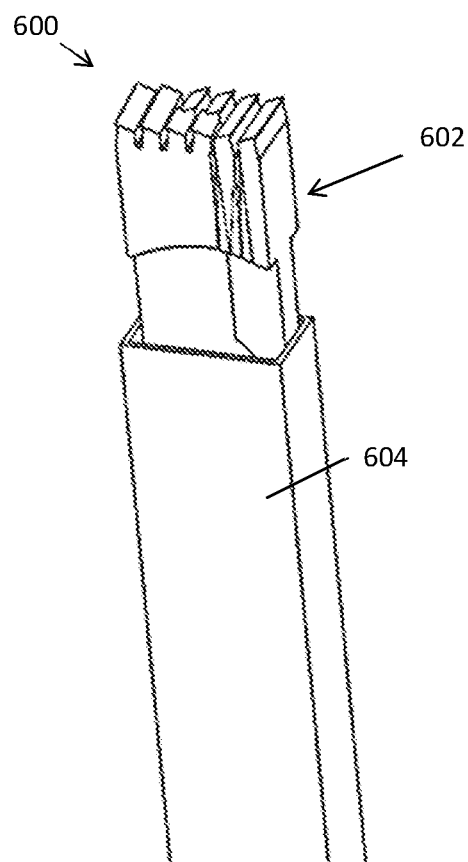

In a particular embodiment and referring to FIGS. 9A-9F, a cutting device 600 to cut, rub, or otherwise remove material 108 around the implant 300 without having to initially gain access into the intramedullary canal (IC) is shown. The cutting device 600 is configured to remove material 108 from an implant by travelling along or just underneath the surface of the implant. The cutting device 600 is particularly thin to remove material 108 directly at the interface between the implant 100 and the material 108. With reference to FIG. 9A, a particular inventive embodiment of the cutting device 600 is shown. The cutting device 600 generally including a pair of scissors 602, and a flexible sheath 604 surrounding internal components of the cutting device 600. In more detail, as shown in FIG. 9B, the scissors 602 includes at least two cutting blades (606a, 606b) each having a plurality of cutting teeth (608a, 608b) located on a distal end of each blade (606a, 606b). The blades (606a, 606b) are pivotally attached at a pivot point 610. The cutting device 600 further includes a spring frame 612, and a drive shaft 614 having an elongated shaft 616 for driving a cam 618. In a detailed view 611, the spring frame 612 includes a plurality of connecting projections 620, a plurality of holding projections 622, and an opening 624. The opening 624 receives a portion of the drive shaft 614. The cam 618 is in mechanical communication with a portion of the blades (606a, 606b). The holding projections 622 act as a clip to secure the driving shaft 614 in place. The plurality of connecting projections 620 are configured to removably couple to the blades and act as a spring during the operation of the cutting device 600. In a particular embodiment, the connecting projections 620 connect to an outer surface of the blades (606a, 606b). While in other embodiments, the connecting projections 620 connect to an inner surface of the blades (606a, 606b)

In various embodiments, the driving shaft 614 is attached to a drill, motor, or other actuator to rotate the drive shaft 614 and therefore the cam 618. As the cam 618 rotates, the blades (606a, 606b) are rapidly pivoted relative to one another, creating a scissoring action. In one embodiment, the cam 618 is oval-shaped. When the longer axis of the oval-shaped cam 618 contacts the blades (606a, 606b), the blades (606a, 606b) are forced apart. Then, as the cam 618 rotates towards the shorter axis of the cam 618, the connecting projections 620 act as a spring forcing the blades (606a, 606b) back towards one another. This creates the scissoring action of the blades (606a, 606b), where the plurality of cutting teeth (608a, 608b) cut, rub, and/or otherwise remove material 108 surrounding an implant.

Figure 9E:
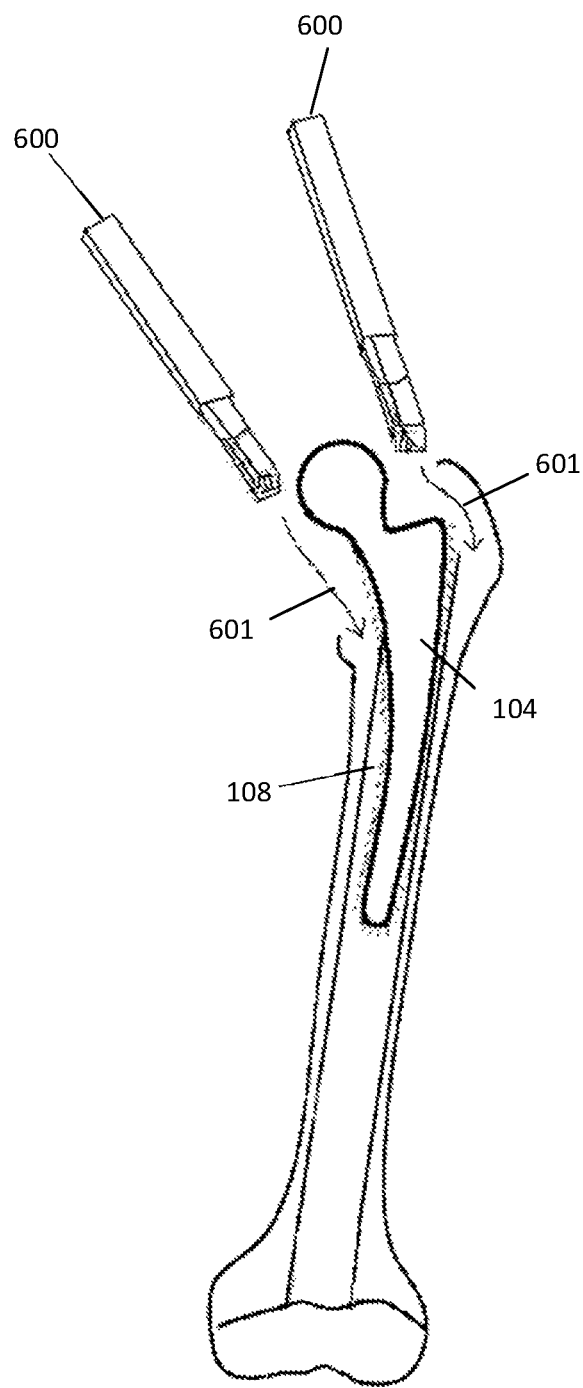
Figure 9F:
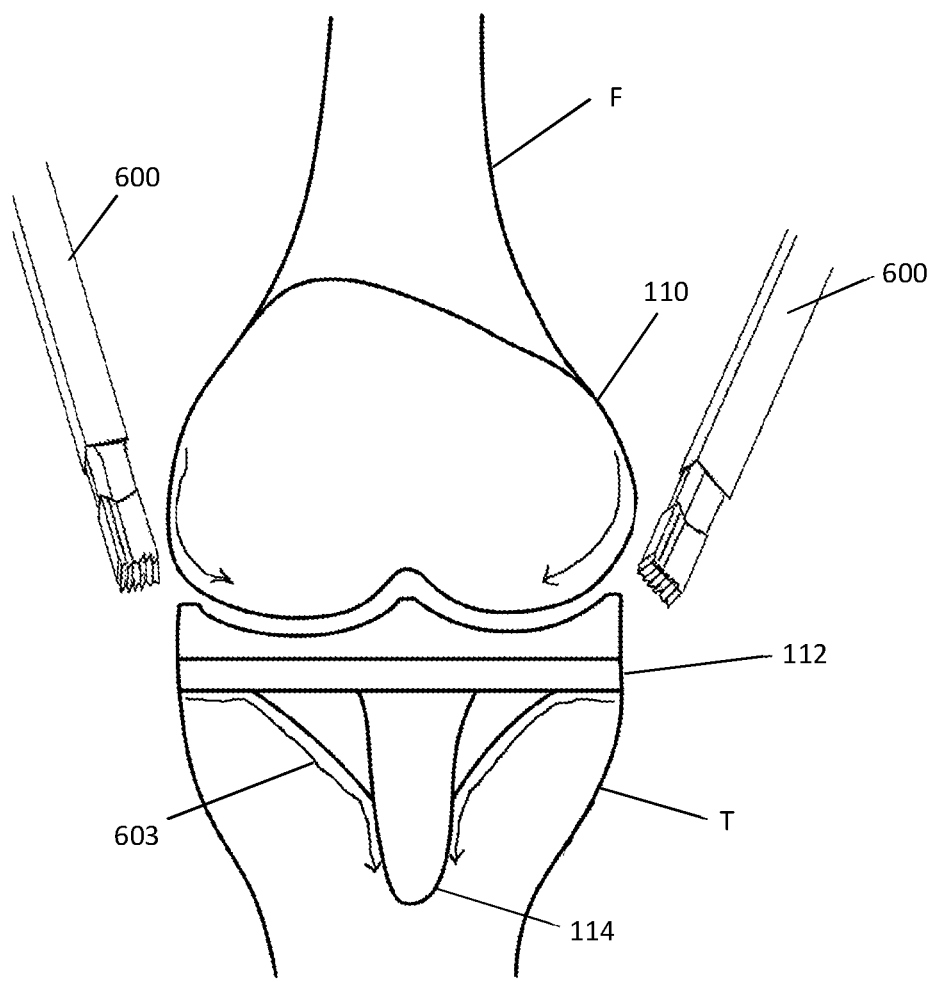

In various embodiments, the cutting device 600 is made out of a flexible and durable material such as nitinol. The cutting teeth (608a, 608b) and other components may be made of a stiffer material, such as stainless steel, to create enough force to remove the material 108 surrounding an implant and/or to drive the components of the cutting device 600. In a particular embodiment, the cutting device 600 is particularly thin, on the order of 1-5 mm in thickness, and 3-7 mm wide so as to sufficiently cut between the material 108 surrounding the implant without having to remove too much bone stock. In addition, the flexibility and strength of the cutting device 600 is of particular importance. The cutting device 600 needs to be flexible, yet strong enough to travel along the length of an implant and into hard-to-reach anatomical areas. For example, FIG. 9E depicts the cutting device 600 cutting around the femoral implant 100 beginning at a proximal part of the femur (F) and following the path of the arrows 601 along the implant 100 interface and down into the intramedullary canal (IC). Likewise, FIG. 9F depicts the cutting device 600 cutting around the components of a total knee implant, which are a femoral knee component 110 installed on the distal portion of the femur F and a tibial knee component 112 installed on the proximal portion of the tibia T. Specifically, the cutting device 600 is capable of removing material down the length of a keel 114 (path shown by arrows 603) of the tibial knee component 112, which is otherwise a very difficult region to remove material 108 from in traditional revision TKA.

In various embodiments, the plurality of cutting teeth (608a, 608b) of the blades (606a, 606b) are designed and angled to grab the material 108 during cutting such the cutting device 600 is pulled deeper into the bone. In other words, as the cutting device 600 operates, the scissoring action of the cutting teeth (608a, 608b) force the cutting teeth (608a, 608b) deeper into the material 108.

Figure 10A:
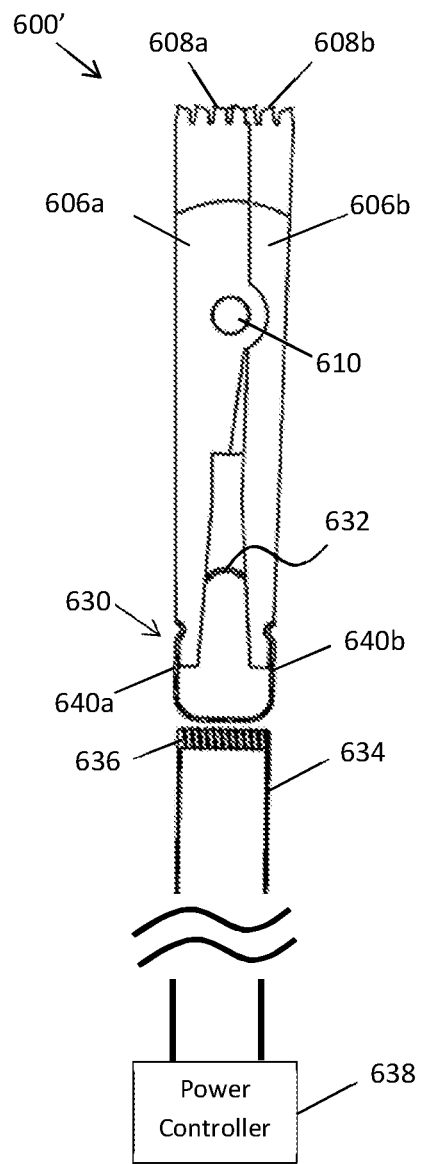
FIGS. 10A-10B depict an inventive cutting device for cutting material directly surrounding an implant using a ferromagnetic shape memory material mechanism in accordance with embodiments of the invention, where
Figure 10B:
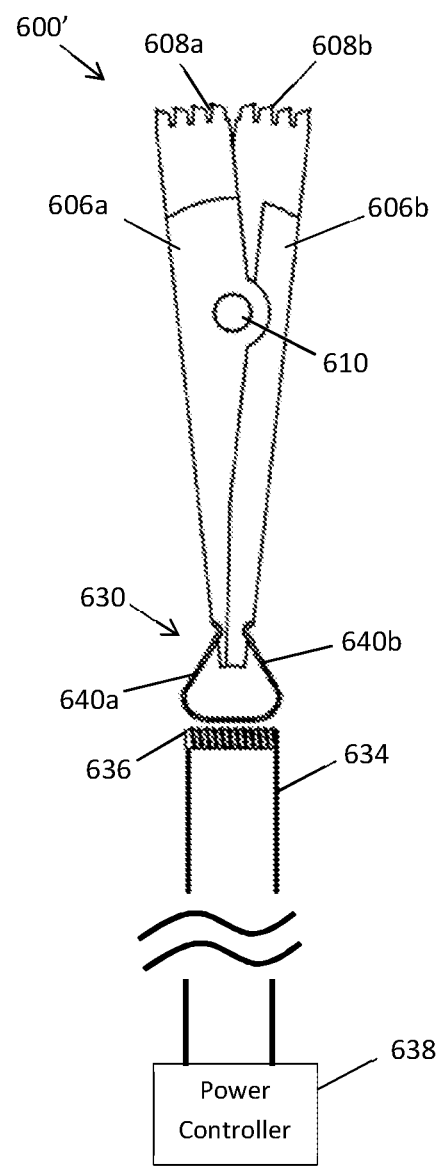

With reference to FIGS. 10A and 10B, a specific inventive embodiment of a cutting device 600' is shown. The cutting device 600' is configured to operate in a similar manner as cutting device 600; however, the mechanism for driving the blades (606a, 606b) is different. Cutting device 600' includes a ferromagnetic shape memory actuator (FSMA) 630, a spring 632, a conductive wire 634 coiled around a core 636, a sheath 604 (as shown in FIG. 9A) surrounding the actuating components and wire 634, and a power controller 638 in electrical communication with the wire 634. The FSMA 630 is configured to exert a force onto a portion of the blades (606a, 606b) in the presence of a magnetic field. The FSMA 630 may be made of an alloy of Nickel, Manganese and Gallium (Ni—Mn—Ga) or equivalent alloys capable of exhibiting a ferromagnetic shape memory effect. In a particular embodiment, the FSMA 630 is in the form of two connected fingers (640a, 640b), where each finger (640a, 640b) interfaces, attaches, or is otherwise in mechanical communication with each blade (606a, 606b). The FSMA 630 may be treated to be in a deformable 'open' state as shown in FIG. 10A, and in an activated 'closed' state as shown in FIG. 10B in the presence of a magnetic field. Therefore, when a magnetic field is present, the FSMA 630 pinches a bottom portion of the blades below the pivot point 610, which drives the cutting teeth (608a, 608b) away from one another. If the cutting teeth (608a, 608b) are angled outward from a center axis of the cutting device 600', activation of the FSMA 630 causes the teeth (608a, 608b) to cut, rub, chip, or otherwise remove material 108 surrounding the implant. Once the magnetic field is removed, the FSMA is in a deformable state, where the spring 632 forces the fingers (640a, 640b) back 'open'. Thus, with the induction and removal of the magnetic field, the blades (606a, 606b) actuate accordingly.

The power controller 638 controls current flowing through the wires 634 and therefore the selective induction of a magnetic field near the FSMA 630. The power controller 638 may pulse direct current to induce and remove the magnetic field at a desired pulse frequency to actuate the blades at desired frequency. In another embodiment, the power controller 638 controls the frequency of alternating current to control the presence/absence of a magnetic field. The power controller 638 may control the frequency of alternating current up to 1000 Hz to cause the blades to actuate at approximately 1000 Hz. In a specific embodiment, the frequency is chosen to match the resonance frequency of the surrounding material 108 to optimize cutting of specific materials.

It should be appreciated, that although the FSMA 630 is shown having an active 'closed' state, the FSMA 630 may be treated to have an active 'open' state, where the FSMA 630 forces the bottom portion of the blades (606a, 606b) (i.e. below the pivot point 610) away from one another in the presence of a magnetic field. In such a case, the teeth (608a, 608b) may be angled inward towards a center axis of the cutting device 600' to cut material upon activation, and the spring 632 biased to pull the bottom portion of the blades (606a, 606b) toward one another in the absence of a magnetic field.

In a particular embodiment, if the power controller 638 and wire 634 coiled around the core 636 is unable to produce a magnetic field of sufficient strength to activate the FSMA 630, a magnetic field may be induced externally. For example, the knee of a patient may be situated inside an external magnetic coil to selectively induce a magnetic field to actuate the blades (606a, 606b) to remove total knee arthroplasty implant components.

There are a couple advantages of the cutting device 600' as compared to cutting device 600. For one, the cutting device 600' no longer requires a rigid drive shaft 614 for driving the blades (606a, 606b), which greatly increases the flexibility and capabilities of the device 600'. Second, the blades (606a, 606b) may be actuated at a much higher frequency, with greater control and safety.

Robotic Procedure

Embodiments of the present invention may also utilize a computer assisted surgical system and a patient specific surgical plan to create a precise plan and procedure for removing an implant from the femur. With reference to FIG. 11, various embodiments of a method for removing an implant in revision surgery with the aid of a surgical system is shown. The method depicts the steps of (a) receiving scan data of a subject's bone S210; (b) creating a virtual three-dimensional model of the subject's bone S220; (c) identifying a precise location to enter the intramedullary canal of the knee S230; (d) registering the location of the target bone and knee intraoperatively S240; (e) robotically milling the target bone S250; (f) inserting the cutting device inside the target bone S260; (g) cutting the cement around the implant S270; (h) removing the implant from the target bone S280. Specific embodiments of the method and components are further described in details below.

The bone models are obtained (Block S210-S220) by generating a three-dimensional (3-D) bone model from an image data set of the subject's anatomy. The image data set may be collected with an imaging modality such as computed tomography (CT), dual-energy x-ray absorptiometry (DEXA), magnetic resonance imaging (MRI), X-ray scans, ultrasound, or a combination thereof. The 3-D bone model(s) are readily generated from the image data set using medical imaging software such as Mimics® (Materialise, Plymouth, Mich.) or other techniques known in the art such as the one described in U.S. Pat. No. 5,951,475. Scan data of the subject's bone may include any of the structural/anatomical features such as size, shape, thickness, and curvatures. Besides structural features, the scan data may include additional bone property data including bone density and bone microarchitecture data. The scan data may be collected by a system and process described herein by a system and process specific to the bone imaging technique.

The user is able to view and manipulate the bone model and bone property data in a pre-operative planning software program having a graphical user interface (GUI). The GUI includes widgets and other tools which allow a user or computer assisted surgical system to customizably design a plan for revising the implant, including removing the primary implant with the devices and methods described herein, and prepare the cavity for a new implant. A robotic system for executing the cut plan is further described below.

A computer-assisted surgical system capable of removing an implant with such precision is desirable. Examples of a computer-assisted surgical system include a 1-6 degree of freedom hand-held surgical system, an autonomous serial-chain manipulator system, a haptic serial-chain manipulator system, a parallel robotic system, or a master-slave robotic system, as described in U.S. Pat. Nos. 5,086,401, 7,206,626, 8,876,830 and 8,961,536, U.S. Pat. App. No. 2013/0060278, and PCT Intl. App. No. US2015/051713.

Figure 12:
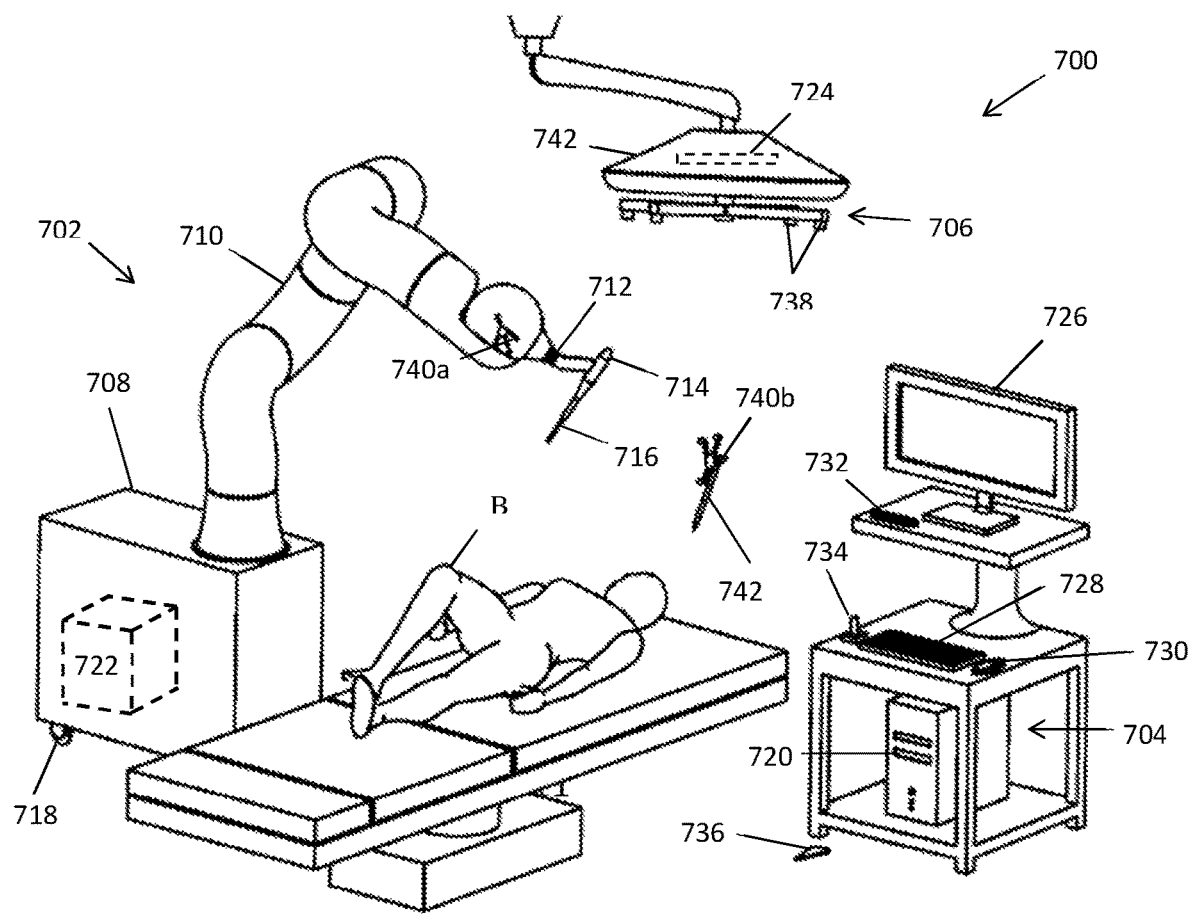
FIG. 12 illustrates a surgical system in the context of an operating room (OR) for executing a revision procedure in accordance with embodiments of the invention.

With reference to FIG. 12, a particular embodiment of a robotic surgical system 700 to remove an implant and revise an orthopedic implant procedure is shown in the context of an operating room (OR). The surgical system 700 generally includes a surgical robot 702, a computing system 704, and a tracking system 706.

The surgical robot 702 includes a movable base 708, a manipulator arm 710 mounted to the base 708, an end-effector flange 712 located at a distal end of the manipulator arm 710, an end-effector assembly 714 removably attached to the flange 712, and a tool 716 removably assembled to the end-effector assembly 714. The base 708 may include a set of wheels 718 to maneuver the base 708, which may be fixed into position using a braking mechanism such as a hydraulic brake. The manipulator arm 710 includes various joints and links to manipulate the tool 716 in various degrees of freedom. The joints may be prismatic, revolute, or a combination thereof. The tool 716 may be any device to contact, perform work or install an implant on the subject's anatomy including for example a burr, a saw, an end-mill, a cutter, a laser engraver, forceps, a claw, electrocautery device, a drill, a pin driver, a reamer, an ultrasonic horn, or a probe. The tool 716 and manipulator are controlled by commands from the computing system 704 and/or tracking system 706. In various embodiments, the tool 716 is the cutting device (300, 600).

The computing system 704 generally includes a planning computer 720 including a processor; a device computer 722 including a processor; a tracking computer 724 including a processor; and peripheral devices. Processors operate in system 700 to perform computations associated with the inventive method. It is appreciated that processor functions are shared between computers, a remote server, a cloud computing facility, or combinations thereof. The planning computer 720, device computer 722, and tracking computer 724 may be separate entities as shown, or it is contemplated that their operations may be executed on just one or two computers depending on the configuration of the surgical system 700. For example, the tracking computer 724 may have the operational data to control the manipulator 710 and tool 716 of the surgical system 700 without the need for a device computer 722. Or, the device computer 722 may include operational data to plan the surgical procedure and design the implant without the need for the planning computer 720. In any case, the peripheral devices allow a user to interface with the surgical system components and may include: one or more user-interfaces, such as a display or monitor 726; and user-input mechanisms, such as a keyboard 728, mouse 730, pendent 732, joystick 734, foot pedal 736, or the monitor 726 may have touchscreen capabilities.

The planning computer 720 contains hardware (e.g., processors, controllers, and memory), software, data and utilities that are dedicated to the implant design and planning of a surgical procedure, either pre-operatively or intra-operatively. This may include reading medical imaging data, segmenting imaging data, constructing three-dimensional (3D) virtual models, storing computer-aided design (CAD) files, and generating surgical plan data. The final surgical plan includes a set of instructions to insert a cutting device in a desirable location, cutting the cement or any material around the implant, removing an implant from the bone, and intra-operative operational data for revising and/or cutting the bone for a new implant, such as a cut-file. The data generated from the planning computer 720 is readily transferred to the device computer 722 and/or tracking computer 724 through a wired or wirelessly connection in the operating room (OR); or transferred via a non-transient data storage medium (e.g., a compact disc (CD), a portable universal serial bus (USB) drive) if the planning computer 514 is located outside the OR.

The device computer 722 may be housed in the moveable base 708 and contain hardware, software, data and utilities that are primarily dedicated to the operation of the surgical robot 702. This may include surgical device control, robotic manipulator control, the processing of kinematic and inverse kinematic data, the execution of registration algorithms, the execution of calibration routines, the execution of surgical plan data, coordinate transformation processing, providing workflow instructions to a user, and utilizing position and orientation (POSE) data from the tracking system 706.

The tracking system 706 of the surgical system 700 includes two or more optical receivers 738 to detect the position of fiducial markers (e.g., retroreflective spheres, active light emitting diodes (LEDs)) uniquely arranged on rigid bodies. The fiducial markers arranged on a rigid body are collectively referred to as a fiducial marker array 740, where each fiducial marker array 740 has a unique arrangement of fiducial markers, or a unique transmitting wavelength/frequency if the markers are active LEDs. An example of an optical tracking system is described in U.S. Pat. No. 6,061,644. The tracking system 706 may be built into a surgical light 742, located on a boom, a stand, or built into the walls or ceilings of the OR. The tracking system computer 724 may include tracking hardware, software, data and utilities to determine the POSE of objects (e.g., bones B, surgical robot 702) in a local or global coordinate frame. The POSE of the objects is collectively referred to herein as POSE data, where this POSE data is readily communicated to the device computer 722 through a wired or wireless connection. Alternatively, the device computer 722 may determine the POSE data using the position of the fiducial markers detected from the optical receivers 738 directly.

The POSE data is determined using the position data detected from the optical receivers 738 and operations/processes such as image processing, image filtering, triangulation algorithms, geometric relationship processing, registration algorithms, calibration algorithms, and coordinate transformation processing. For example, the POSE of a digitizer probe 742 with an attached probe fiducial marker array 740*b* may be calibrated such that the probe tip is continuously known as described in U.S. Pat. No. 7,043,961. The POSE of the tool tip or tool axis of the tool 716 may be known with respect to a device fiducial marker array 740*a* using a calibration method as described in U.S. Prov. Pat. App. 62/128,857. The device fiducial marker 740*a* is depicted on the manipulator arm 710 but may also be positioned on the base 708 or the end-effector assembly 714. Registration algorithms are readily executed to determine the POSE and coordinate transforms between a bone B, a fiducial marker array 740, the surgical robot 702, the and the surgical plan, using registration methods known in the art, such as those described in U.S. Pat. Nos. 6,033,415, and 8,287,522.

The POSE data is used by the computing system 704 during the procedure to update the POSE and coordinate transforms between the bone B, the surgical robot 702, and the surgical plan to ensure the surgical robot 702 accurately executes the surgical plan on the bone B. It should be appreciated that in certain embodiments, other tracking systems may be incorporated with the surgical system 700 such as an electromagnetic field tracking system or a mechanical tracking system. An example of a mechanical tracking system is described in U.S. Pat. No. 6,322,567. In a particular embodiment, the surgical system 700 does not include a tracking system 706 and a tracked digitizer probe 742, but instead employs a mechanical digitizer arm incorporated with the surgical robot 702 as described in U.S. Pat. No. 6,033,415, and a bone fixation and monitoring system that fixes the bone directly to the surgical robot 702 and monitors bone movement as described in U.S. Pat. No. 5,086,401, both of which are incorporated by reference herein in their entirety.

Intra-Operative Execution

Intra-operatively, the bone is registered to the workspace of the robot (Block S240). Subsequently, the robotic milling of the target bone is provided at block S250. With reference back to FIG. 2, the system in certain inventive embodiments functions to determine and/or drill the opening 200 at a pre-operatively planned location to gain access to the intramedullary canal (IC). An optimal location for the opening 400 may be determined by analyzing anatomical features of the target bone and where it allows the entrance of an external object (such as the cutting device 300) to the intramedullary canal (IC) of the femur F. In other embodiments, the optimal site for the opening 200 may be determined by analyzing anatomical and biological features of the target bone intra-operatively. It should be appreciated that if the locations, size, and shape of the opening 200 was pre-operatively planned, the location, shape, and size of the opening 200 may be changed prior to drilling the opening 200 by a user or a surgeon based on intra-operative anatomical measurements of each individual patient. Further, it should be appreciated that although the milling to create the opening 200 is done by the robotic system, the opening 200 may be created manually by a user at any time during the procedure.

The robotic cutting of material 108 around the implant is provided at block S270. In various embodiments, with reference back to FIG. 5D, the surgical robot 702 may insert and operate the aforementioned cutting device (300, 600) inside the intramedullary canal (IC) of the femur, F. The end effector assembly 714 may include a motor or other actuator to drive the rotation and translation of the cutting device 300 around and along the length of the implant 100. If necessary, the cutting may be interrupted at any time during the surgery by a user or a surgeon. The cutting continues until the user is able to safely remove the primary implant from the bone.

After the user removes the implant, the surgical system 702 may prepare the bone to receive the revision components. During the pre-operative planning, the user may plan a desired POSE for the revision components based on the cavity that remains after the removal of the primary components. Because the geometry of the cutting device (300, 600) is known, particularly the thickness of the cutting device (300, 600), the geometry of the cavity after removal is also known. Therefore, the user can plan the placement of the new components based on the expected cavity dimensions. This is particularly advantageous because with traditional revision surgeries, the resulting cavity after removal of the primary implant is completely unknown and therefore pre-operatively planning the procedure is nearly impossible. Thus, the robotic system 700 allows a user to plan and precisely prepare a new cavity for the new components, greatly improving the stability and longevity of the revision components.

The invention claimed is:

1. A cutting device for removing material directly surrounding an outer surface of an implant in an intramedullary canal of a target bone, the cutting device comprising:
   an expandable tube having a base and a hollow interior for receiving the implant therein, the expandable tube comprising:
      a plurality of cutting segments extending from the base and terminating to form a distal end of the expandable tube, at least one cutting segment of the plurality of cutting segments having a cutting end with a plurality of cutting teeth at the distal end of the expandable tube; and
      a plurality of spring shaped sections extending between the plurality of cutting segments.

2. The cutting device of claim 1 wherein the plurality of spring shaped sections couple at least a portion of the plurality of cutting segments together.

3. The cutting device of claim 1 wherein each of the spring shaped sections of the plurality of spring shaped sections are interspersed with at least two of said plurality of cutting segment and removable from the cutting device.

4. The cutting device of claim 1 wherein the plurality of spring shaped sections includes a first removable spring shaped section of a first size and a second removable spring shaped section of a second size different than the first size.

5. The cutting device of claim 1 wherein the cutting device is manufactured from a single piece of material and has edges that have characteristics of a plasma or laser cut.

6. The cutting device of claim 1 wherein the cutting device is formed of nitinol.

7. The cutting device of claim 1 wherein each of the cutting ends of the plurality of cutting ends are adapted to be removably coupled to the plurality of cutting segments.

8. The cutting device of claim 1 wherein the cutting ends are made of a material that is stiffer than the cutting segments.

9. The cutting device of claim 1 wherein the base of the cutting device is configured to couple directly to a drill, which drives rotation of the cutting device.

10. The cutting device of claim 1 wherein the base of the expandable tube is adapted to be coupled to a vacuum source.

* * * * *